(12) United States Patent
Gilbert

(10) Patent No.: US 8,610,501 B2
(45) Date of Patent: Dec. 17, 2013

(54) CLASS RESONANT-H ELECTROSURGICAL GENERATORS

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 946 days.

(21) Appl. No.: 12/619,234

(22) Filed: Nov. 16, 2009

(65) Prior Publication Data

US 2011/0115562 A1    May 19, 2011

(51) Int. Cl.
*H03F 3/217*    (2006.01)

(52) U.S. Cl.
USPC ..................................... 330/251; 330/207 A

(58) Field of Classification Search
USPC ........................................ 330/10, 251, 207 A
See application file for complete search history.

(56) References Cited

U.S. PATENT DOCUMENTS

| | | | |
|---|---|---|---|
| 4,430,625 A | 2/1984 | Yokoyama | |
| 5,396,194 A | 3/1995 | Williamson et al. | |
| 5,438,302 A | 8/1995 | Goble | |
| 5,777,519 A | 7/1998 | Simopoulos | |
| 6,093,186 A | 7/2000 | Goble | |
| 6,104,248 A | 8/2000 | Carver | |
| 6,293,942 B1 | 9/2001 | Goble | |
| 6,304,138 B1 | 10/2001 | Johnson | |
| 6,538,909 B2 * | 3/2003 | Goodarzi et al. | 363/98 |
| 7,422,582 B2 | 9/2008 | Malackowski et al. | |
| 2008/0122408 A1 * | 5/2008 | Keiter et al. | 322/28 |
| 2008/0310046 A1 | 12/2008 | Menegoli | |
| 2012/0176084 A1 * | 7/2012 | Klaes | 320/107 |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |

(Continued)

OTHER PUBLICATIONS

U.S. Appl. No. 10/406,690, filed Apr. 3, 2003.

(Continued)

*Primary Examiner* — Henry Choe

(57) ABSTRACT

A generator for use with an electrosurgical device is provided. The generator has a gain stage electrically disposed between a first voltage rail and a second voltage rail, wherein the gain stage includes an input and an output. A voltage source operably coupled to the gain stage input and configured to provide an input signal thereto responsive to a drive control signal is also provided. The generator also has one or more sensors configured to sense an operational parameter of the amplifier and to provide a sensor signal corresponding thereto and a controller adapted to receive the sensor signal(s) and in response thereto provide a drive control signal to the voltage source. The generator has an amplifier output configured to supply an output voltage corresponding to the first voltage rail and the second voltage rail when the output of the gain stage falls between a voltage of the first voltage rail and a voltage of the second voltage rail and is configured to supply a peak voltage output when the voltage output is falls greater than the voltage of the first voltage rail or less than the voltage of the second voltage rail.

7 Claims, 7 Drawing Sheets

(56) References Cited

FOREIGN PATENT DOCUMENTS

| | | |
|---|---|---|
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 2154481 | 9/1985 |
| SU | 166452 | 1/1965 |
| SU | 727201 | 4/1980 |
| WO | WO 98/27880 | 7/1998 |
| WO | WO 02/11634 | 2/2002 |
| WO | WO 02/45589 | 6/2002 |
| WO | WO 03/090635 | 11/2003 |
| WO | WO 2006/050888 | 5/2006 |

OTHER PUBLICATIONS

U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.
U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
International Search Report EP10191319 dated Feb. 22, 2011.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. Ml, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
Erickson et al., "Fundamentals of Power Electronics Second Edition", Springer Science, 2001, ISBN 0-7923-7270-0.
Raab et al., RF & Microwave Power Amplifier & Transmitter Technologies—Part 3 and 5 (pp. 40, 42 and 46).
Leach Jr., "The Class-D Amplifier", Introduction to Electroacoustics and Audio Amplifier Design, Second Edition, 2001 (pp. 1-6).
International Search Report EP 98300964.8 dated Dec. 4, 2000.
International Search Report EP 04009964 dated Jul. 13, 2004.
International Search Report EP 04011375 dated Sep. 10, 2004.

(56) References Cited

OTHER PUBLICATIONS

International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/USO4/13443 dated Dec. 10, 2004.
International Search Report PCT/US09/46870 dated Jul. 21, 2009.

\* cited by examiner

CLASS RESONANT-H ELECTROSURGICAL GENERATORS

BACKGROUND

1. Technical Field

The present disclosure relates to systems for providing energy to biological tissue and, more particularly, to improved apparatus for amplifying energy for use during electrosurgical procedures.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually having elongated cylindrical geometry) are inserted into a living body and placed in the tumor region of an affected organ. A typical form of such needle electrodes incorporates an insulated sheath from which an exposed (uninsulated) tip extends. When an RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned immediately adjacent the electrodes. When the electrodes are sufficiently separated from one another, the electrical circuit is open and thus inadvertent contact with body tissue with either of the separated electrodes does not cause current to flow.

Commonly used power amplifiers are known to be inefficient. For example, a class A/B microwave power amplifier typically exhibits an efficiency of about 35%. That is, to achieve a surgical signal of 250 W, a class A/B power amplifier requires about 714 W of power, of which 464 W is dissipated as thermal energy. The resulting heat becomes difficult to manage and may require the use of bulky and costly cooling systems, e.g., fans and heat sinks. Additionally, the excess heat may cause thermal stress to other components of the generator, shortening generator life, decreasing reliability, and increasing maintenance costs. Additionally, a class A/B amplifier may exhibit crossover distortion that introduces undesirable harmonics into the surgical signal, which are known to cause radiofrequency interference in excess of acceptable limits.

Because electrosurgery requires very large ranges of voltage and current while maintaining a very high conversion efficiency to reduce the size and heat sink needs, some electrosurgical devices use a tuned resonance circuit driven by a class C or class E output. However, such an arrangement has a disadvantage in that the quality factor or Q factor changes with the load applied to the circuit making it difficult to maintain the desired voltage or current at the output. A manifestation of this disadvantage may be excessive or undesired "ringing" at the output for underdamped or high Q situations of loading. Class A/B outputs do not suffer from this disadvantage because their output impedances are typically much lower.

SUMMARY

The present disclosure provides an apparatus for a generator. In accordance with the present disclosure, the generator includes a gain stage electrically disposed between a first voltage rail and a second voltage rail, wherein the gain stage includes an input and an output, a voltage source operably coupled to the gain stage input and configured to provide an input signal thereto responsive to a drive control signal, at least one sensor configured to sense an operational parameter of the amplifier and to provide a sensor signal corresponding thereto, a controller adapted to receive the at least one sensor signal and in response thereto provide the drive control signal to the voltage source. An amplifier output is provided and configured to supply an output voltage corresponding to the first voltage rail and the second voltage rail when the output of the gain stage falls between a voltage of the first voltage rail and a voltage of the second voltage rail and is configured to supply a peak voltage output when the voltage output is greater than the voltage of the first voltage rail or less than the voltage of the second voltage rail.

In other embodiments, the gain stage further comprises a class A/B amplifier having at least two gain elements arranged in a push-pull configuration. The at least two gain elements are selected from the group consisting of bipolar transistors, field-effect transistors, and laterally diffused metal oxide semiconductors. The sensor is configured to sense an output voltage or a bias current. The gain stage may also include a bias circuit where the controller operably couples to the bias circuit and is configured to provide a bias voltage thereto responsive to a bias control signal and wherein the controller provides a bias control signal to the bias controller in response to the at least one sensor signal.

In another embodiment, an electrosurgical generator is provided having a voltage source, a gain stage, a class resonant-H amplifier, at least one switch, and a controller operable to control an output of the voltage source and control the at least one switch based on a pulse width modulated signal. The at least one switch may be a field effect transistor. The electrosurgical generator may also include at least one sensor operable to sense an operational parameter of the amplifier and to provide a sensor signal corresponding thereto.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The generator according to the present disclosure can perform ablation, monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
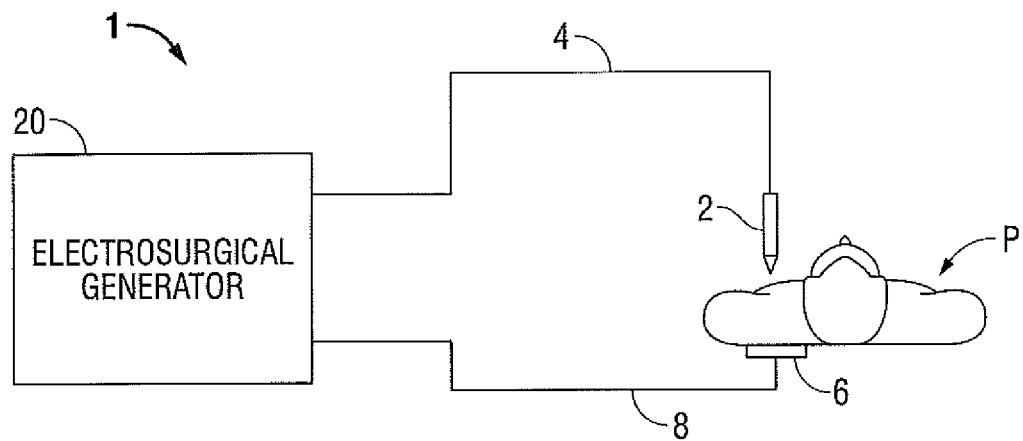
FIGS. 1A-1B are schematic block diagrams of an electrosurgical system according to the present disclosure for use with various instrument types.

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via a supply line 4, which is connected to an active terminal 212 (FIG. 7) of the generator 20, allowing the instrument 2 to coagulate, ablate and/or otherwise treat tissue. The energy is returned to the generator 20 through a return electrode 6 via a return line 8 at a return terminal 211 (FIG. 7) of the generator 20. The active terminal 212 and the return terminal 211 are connectors configured to interface with plugs (not explicitly shown) of the instrument 2 and the return electrode 6, which are disposed at the ends of the supply line 4 and the return line 8, respectively.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

Figure 1B:
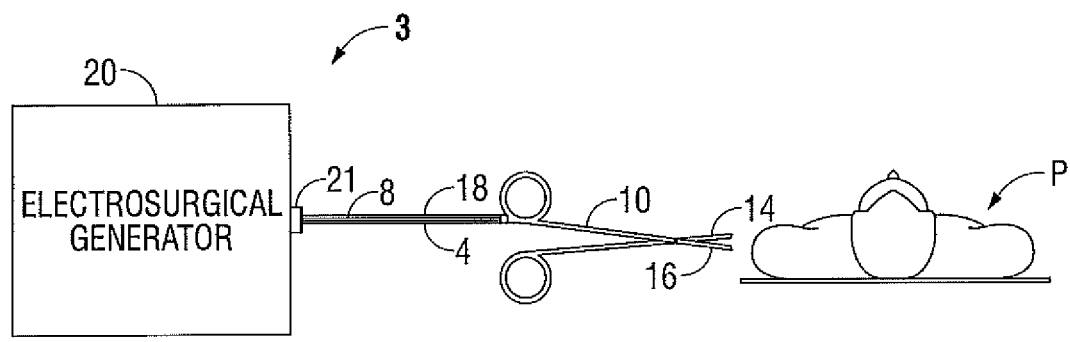
Figure 7:
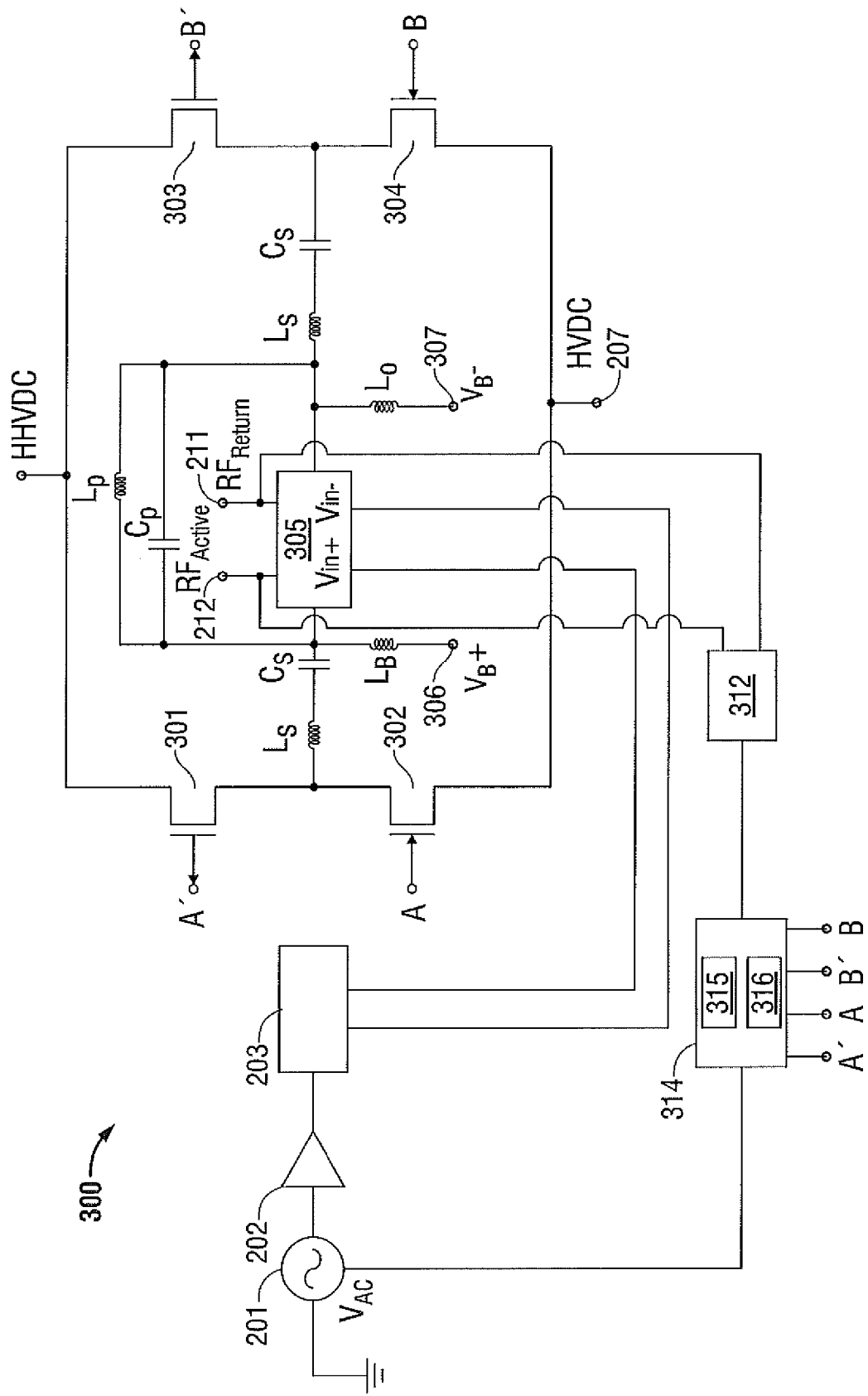
FIG. 7 is a schematic block diagram of a generator according to another embodiment of the present disclosure.

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 include opposing jaw members having an active electrode 14 and a return electrode 16, respectively, disposed therein. The active electrode 14 and the return electrode 16 are connected to the generator 20 through cable 18, which includes the supply and return lines 4, 8 coupled to the active and return terminals 212, 211, respectively (FIG. 7). The electrosurgical forceps 10 are coupled to the generator 20 at a connector 21 having connections to the active and return terminals 212 and 211 (e.g., pins) via a plug disposed at the end of the cable 18, wherein the plug includes contacts from the supply and return lines 4, 8.

Figure 2:
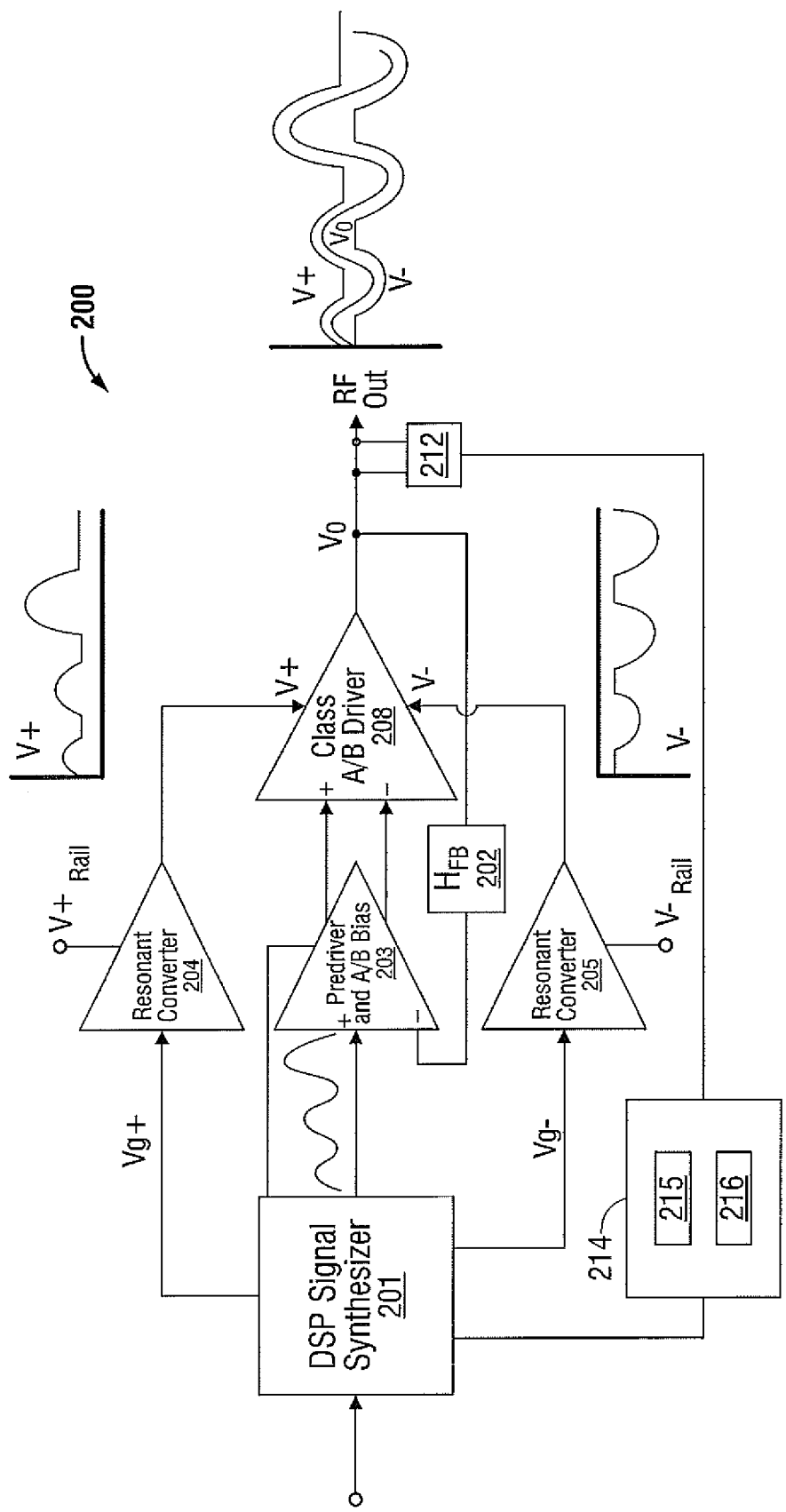
FIG. 2 is a schematic block diagram of a class resonant-H RF electrosurgical generator according to an embodiment of the present disclosure.

FIG. 2 shows a schematic diagram of the generator 20 employing an example of a class resonant-H amplifier 200 in accordance with an embodiment of the present disclosure. A Class H amplifier creates an infinitely variable supply rail. This is done by modulating the supply rails so that the rails are only a few volts larger than the output signal at any given time. The output stage, which is typically a linear class A/B topology, operates at its maximum efficiency all the time. Resonant switched mode converters can be used to create the tracking rails. Significant efficiency gains, especially for sinusoidal waveforms, can be achieved using a class resonant-H amplifier. As shown in FIG. 2, the digital signal processor (DSP) signal synthesizer 201 provides an input voltage and is coupled to bias and predriver amplifier 203. The input voltage has a wave form similar to sine wave, but it is not necessarily limited to a sine wave. The wave form for the input voltage may be a triangular wave, square wave, a series of pulses, a pulse width modulated (PWM) signal or any other waveform used to drive an electrosurgical generator.

Figure 5:
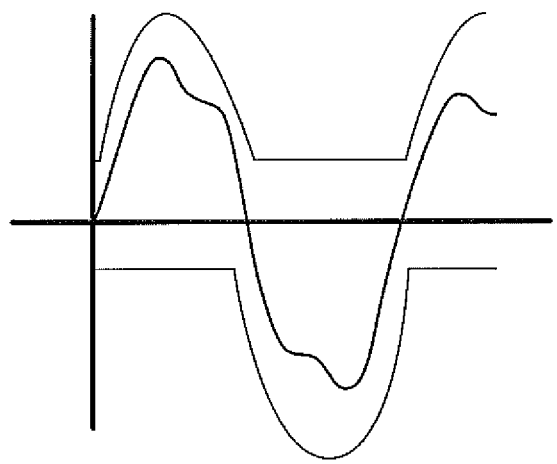
FIG. 5 is a graph representing voltage outputs of the class resonant-H RF electrosurgical generator according to an embodiment of the present disclosure.

However, the best efficiency of the class resonant-H is obtained with sinusoid waveforms. This is graphically exemplified in FIG. 5, where a waveform containing add-order harmonics must be contained within a sinusoidal envelope of the fundamental. This compensation might be performed by the DSP signal synthesizer 201.

The input voltage is fed into voltage gain stage 203, amplifier 204 and amplifier 205 of class resonant-H amplifier 200. Voltage gain stage 203 amplifies the input voltage and provides the amplified voltage as an output to a class A/B amplifier 208. Voltage gain stage 203 may include a transformer to provide patient isolation between the voltage source 201 and the patient. Alternatively, isolation may be provided at the output of the amplifier 200. Voltage gain stage 203 may also include a bias circuit that can be controlled by controller 214 to provide a bias voltage for the class A/B amplifier 208. The combined power amplifier formed by 203 and 208 may be run open-loop or closed-loop. Closed-loop operation may be effected by addition of feedback network 202.

Figure 3:
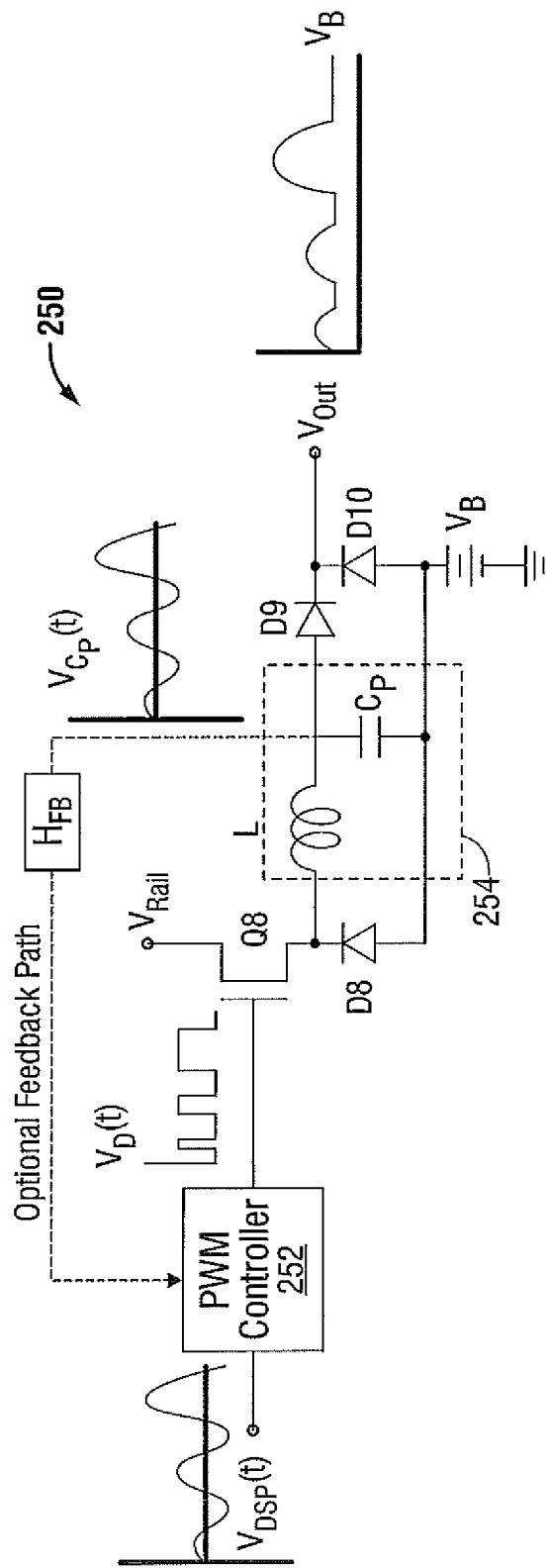
FIG. 3 is a schematic block diagram of a parallel resonant converter according to an embodiment of the present disclosure.

Amplifier 208 may include two transistors in a push-pull configuration and may be a part of the voltage gain stage 203 discrete components. The two transistors in amplifier 208 may be bipolar transistors, field-effect transistors, and laterally diffused metal oxide semiconductors Amplifiers 204 and 205 may be class C, E or F amplifiers or they may be PWM resonant class D amplifiers, an example of which is shown in FIG. 3, PWM resonant class D amplifier 250 receives a signal from DSP signal synthesizer 201 and is inputted into a PWM controller 252 that outputs a PWM signal, shown as $V_g(t)$, to field effect transistor (FET) Q3. The low pass filter 254, comprising inductor L and capacitor $C_P$, passes the average value of the square wave output of Q3 to generate a waveform shown as $V_{CP}(t)$. A voltage source $V_B$ provides a DC offset such that $V_{OUT}$ does not fall below $V_B$. An optional feed back path may be provided that applies a transfer function $H_{FB}$ to $V_{CP}(t)$ before providing the signal to PWM controller 252.

Figure 4:
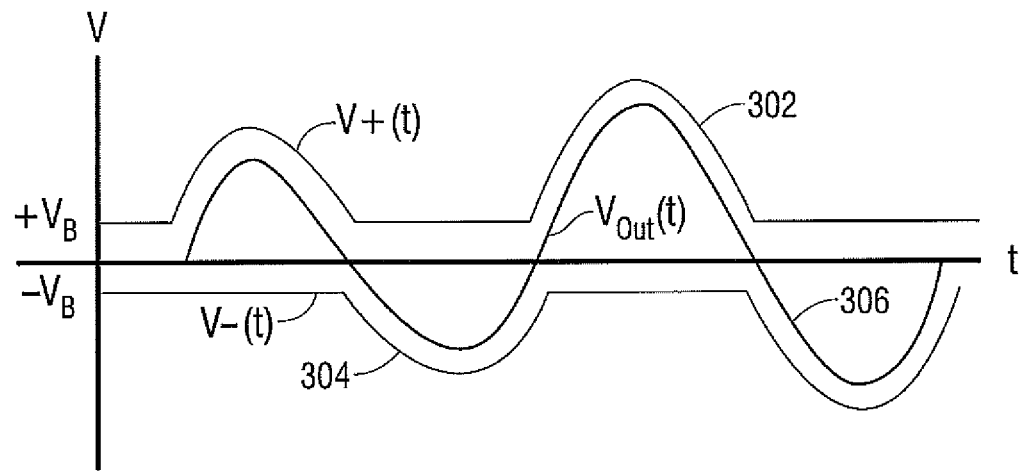
FIG. 4 is a graph representing voltage outputs of the class resonant-H RF electrosurgical generator according to an embodiment of the present disclosure.

Amplifiers 204 and 205 provide a positive voltage and a negative voltage power supply rails as shown in FIG. 4. In FIG. 4, positive voltage power supply rail (+V(t)) 302 and negative voltage power supply rail (−V(t)) 304 track the output voltage 306. As shown in FIG. 4, when the output voltage is less than $+V_B$ or greater than $-V_B$, the output of the amplifier 200 is $+V_B$ or $-V_B$ which is applied to the linear devices in the generator thereby keeping them in a forward bias. When a peak appears in output voltage 306, the supply rails 302 and 304 also peak.

Figure 6:
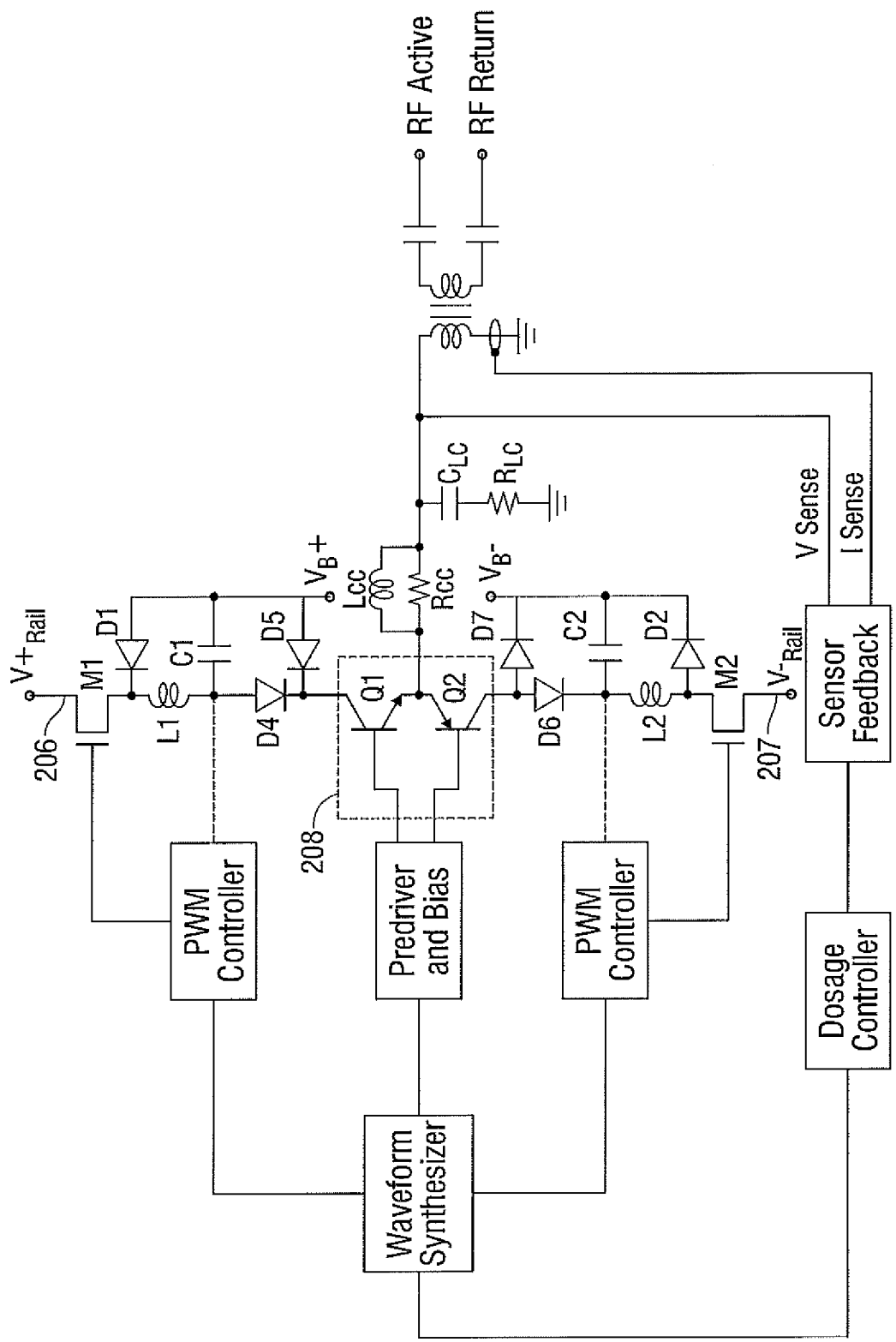
FIG. 6 is a schematic block diagram of a class resonant-H RF electrosurgical generator according to an embodiment of the present disclosure.

A more complete implementation of a class resonant-H RF electrosurgical generator is provided in FIG. 6. During non-peak operation current flows from $+V_B$ and $-V_B$ through diodes D5 and D7 respectively. When a peak appears at the bases of transistors Q1 and Q2 in the class MB amplifier 208, the parallel resonant output of L1, C1 and L2 C2 are alternatively activated by pulse width modulation (see FIG. 3 $V_g(t)$ and $V_{CP}(t)$ waveforms) of switch networks M1, D1 and M2, D2. The AC outputs are in turn rectified by D4 and D6. Inductor $L_{CC}$ and resistor $R_{CC}$ may be included in the RF electrosurgical generator for highly capacitive loads while capacitor $C_{LC}$ and resistor $R_{LC}$ may be included for highly inductive loads.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

In particular, the active terminal 212 generates either continuous or pulsed sinusoidal waveforms of high RF energy. The active terminal 212 is configured to generate a plurality of waveforms having various duty cycles, peak voltages, crest factors, and other suitable parameters. Certain types of waveforms are suitable for specific electrosurgical modes. For instance, the active terminal 212 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of RF energy between the connectors, such that, for instance, when the instrument 2 is connected to the generator 20, only the monopolar plug receives RF energy.

The controller 214 includes a microprocessor 215 operably connected to a memory 216, which may be volatile type memory (e.g., RAM) and/or non-volatile type memory (e.g., flash media, disk media, etc.). The controller 214 includes an output port that is operably connected to a variable DSP signal synthesizer 201, $+V_g$ terminal 221, $-V_g$ terminal 222, +HVDC terminal 206 and/or −HVDC terminal 207 allowing the controller 214 to control the output of the generator 20 according to either open and/or closed control loop schemes. Those skilled in the art will appreciate that the microprocessor 215 may be substituted by any logic processor or analog circuitry (e.g., control circuit) adapted to perform the calculations discussed herein.

The generator 20 may implement a closed and/or open loop control schemes which include a sensor circuit 212 having a plurality of sensors measuring a variety of tissue and energy properties (e.g., tissue impedance, tissue temperature, output current and/or voltage, etc.), and providing feedback to the controller 214. A current sensor can be disposed at either the active or return current path or both and voltage can be sensed at the active electrode(s). The controller 214 then transmits appropriate signals to the DSP signal synthesizer 201, voltage gain stage 203, $+V_g$ terminal 221, $-V_g$ terminal 222, +HVDC terminal 206 and/or −HVDC terminal 207, which then adjust AC or DC power supply, respectively, by using a maximum allowable energy which varies according to the selected mode. The controller 214 also receives input signals from the input controls of the generator 20 or the instrument 2. The controller 214 utilizes the input signals to adjust power output by the generator 20 and/or performs other control functions thereon.

The sensor circuit 212 measures the electrical current (I) and voltage (V) supplied by the active terminal 212 in real time to characterize the electrosurgical process during both the matching sinusoidal and non-sinusoidal durations for a predetermined sampling period, the former being of short duration (e.g., half a cycle) and the latter being of long duration (e.g., 15 cycles). This allows for the measured electrical properties to be used as dynamic input control variables to achieve feedback control. The current and voltage values may also be used to derive other electrical parameters, such as power (P=V*I) and impedance (Z=V/I). The sensor circuit 212 also measures properties of the current and voltage waveforms and determines the shape thereof.

FIG. 7 shows a schematic diagram of an electrosurgical generator 300 in accordance with another embodiment of the present disclosure. The generator 300 has a voltage source 201, buffer 202, a voltage gain stage 203, a +HVDC supply 206 and a −HVDC supply 207 as in generator 20. Further, the generator has a sensor 312 similar to sensor 212 described above and a controller 314 with microprocessor 314 and memory 315 somewhat similar to the controller 214, microprocessor 215 and memory 216 described above with regard to FIG. 2.

Figure 8:
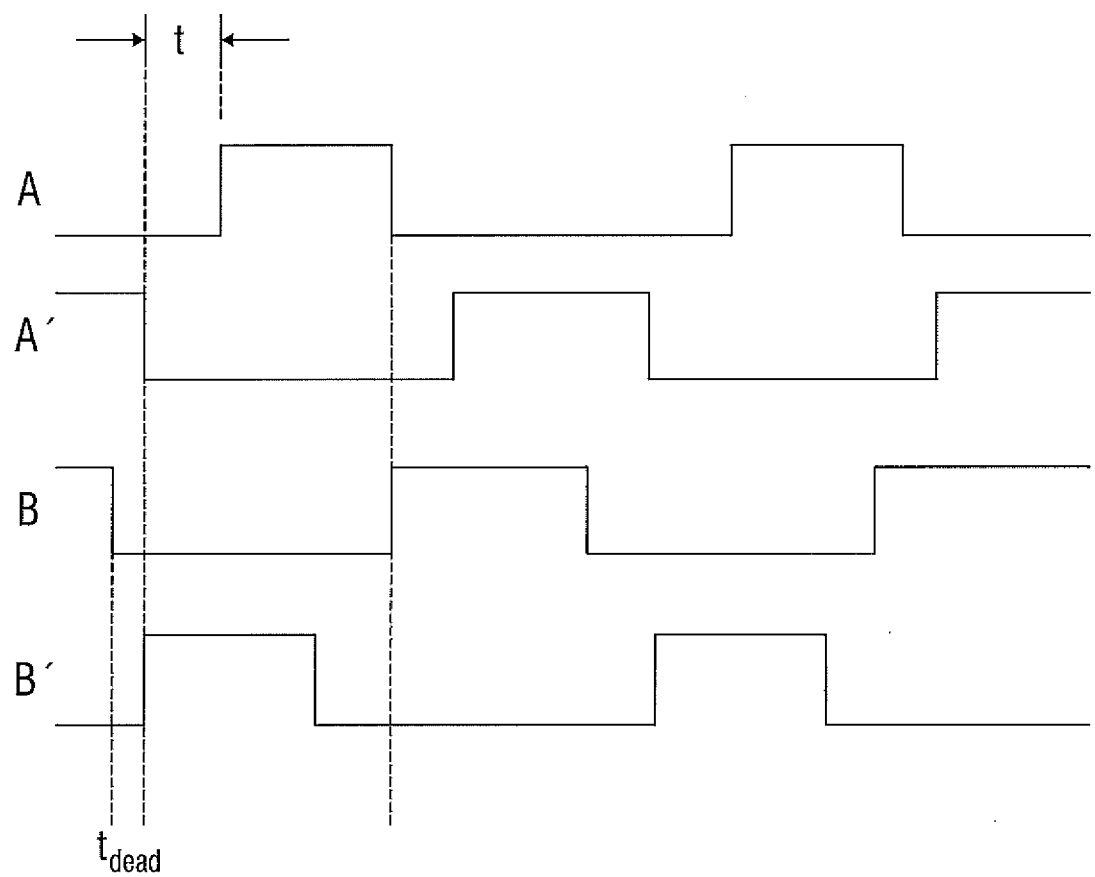
FIG. 8 is a timing chart for the signals applied to the generator of FIG. 7 according to an embodiment of the present disclosure.

In generator 300, the output of the voltage gains stage 203 is fed into the class A/B amplifier 305 at the $+V_{IN}$ and $-V_{IN}$ terminals. Instead of using parallel resonant converters as shown in FIG. 2, generator 300 utilizes series-parallel, or LCLC, converters driven in full-bridge by active field effect transistor (FET) switches 301, 302, 303 and 304. Controller 314 supplies phase-shifted PWM timing signals to FET switches 301, 302, 303 and 304 as shown in FIG. 8. The duty cycle of the PWM signals (e.g., D=0.75) affects the voltage output such that $V_{OUT}$ is proportional to D·HVDC. The duty cycle is determined by the amount of overlap in a phase-shifted PWM converter The current flows from FET 301 to FET 304 when signal A' overlaps signal B and current flows from FET 303 to FET 302 when signal B' overlaps signal A. As shown in FIG. 8, signals A and A' and B and B' are phase shifted 180° and offset by time t.

Components $L_S$, $C_S$, $L_P$ and $C_P$ are selected to provide resonant output amplitudes that are proportional to the phase-shifted PWM duty cycles times the power supply rails HVDC. Terminal 30 supplies a positive voltage bias ($+V_B$) which is a small DC bias voltage that is required to supply bias current to amplifier 305. $+V_B$ is coupled to inductor $L_B$ to provide a float voltage that is supplied to the linear class amplifier 305. A negative voltage bias ($-V_B$) 307 is also coupled to the amplifier 305 to supply bias current to the amplifier 305. An inductor $L_B$ may be coupled between amplifier 305 and terminal 307 based on whether the output is balanced or unbalanced. Inductor $L_B$ is connected when the output is balanced at a low input or quiescent (below $\pm V_B$).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. A generator, comprising:
    a gain stage electrically disposed between a first voltage rail and a second voltage rail, wherein the gain stage includes an input and an output;
    a voltage source operably coupled to the gain stage input and configured to provide an input signal thereto responsive to a drive control signal;
    at least one sensor configured to sense an operational parameter of the amplifier and to provide a sensor signal corresponding thereto;
    a controller adapted to receive the at least one sensor signal and in response thereto provide the drive control signal to the voltage source; and
    an amplifier output configured to supply an output voltage corresponding to the first voltage rail and the second voltage rail when the output of the gain stage falls between a voltage of the first voltage rail and a voltage of the second voltage rail and is configured to supply a peak voltage output when the voltage output is greater than the voltage of the first voltage rail or less than the voltage of the second voltage rail.

2. The generator in accordance with claim 1, wherein the gain stage further includes a class A/B amplifier.

3. The generator in accordance with claim 2, wherein the gain stage comprises at least two gain elements arranged in a push-pull configuration.

4. The generator in accordance with claim 3, wherein the at least two gain elements are selected from the group consisting of bipolar transistors, field-effect transistors, and laterally diffused metal oxide semiconductors.

5. The generator in accordance with claim 1, wherein the sensor is configured to sense an output voltage.

6. The generator in accordance with claim 1, wherein the sensor is configured to sense a bias current.

7. The generator in accordance with claim 6, wherein:
    the gain stage includes a bias circuit and the controller operably couples to the bias circuit and is configured to provide a bias voltage thereto responsive to a bias control signal and wherein the controller provides a bias control signal to the bias controller in response to the at least one sensor signal.

* * * * *